United States Patent [19]

Fabozzi

[11] Patent Number: 5,498,241
[45] Date of Patent: Mar. 12, 1996

[54] WINGED NEEDLE ASSEMBLY WITH PROTECTIVE MEMBER

[75] Inventor: Richard C. Fabozzi, Sligo, Ireland

[73] Assignee: Abbott Laboratories, Abbott Park, Ill.

[21] Appl. No.: 351,844

[22] Filed: Dec. 8, 1994

[51] Int. Cl.⁶ ........................................ A61M 5/32
[52] U.S. Cl. ........................................ 604/177; 604/165
[58] Field of Search ........................ 604/177, 158, 604/165

[56] References Cited

U.S. PATENT DOCUMENTS

| | | | |
|---|---|---|---|
| 4,013,080 | 3/1977 | Froning | 604/165 |
| 4,389,210 | 6/1983 | Genese | 604/177 |
| 4,676,783 | 6/1987 | Jagger et al. . | |
| 4,834,708 | 5/1989 | Pillari | 604/165 |
| 4,941,881 | 7/1990 | Masters et al. | 604/177 |
| 5,069,341 | 12/1991 | Barbieri et al. | 206/365 |
| 5,088,982 | 2/1992 | Ryan . | |
| 5,108,376 | 4/1992 | Bonaldo | 604/177 |
| 5,112,311 | 5/1992 | Utterberg et al. . | |
| 5,120,320 | 6/1992 | Fayngold . | |
| 5,192,275 | 3/1993 | Burns . | |
| 5,219,339 | 6/1993 | Saito | 604/177 |
| 5,266,072 | 11/1993 | Utterberg et al. . | |
| 5,312,359 | 5/1994 | Wallace . | |
| 5,330,438 | 7/1994 | Gollobin et al. | 604/177 |
| 5,382,240 | 1/1994 | Lam | 604/177 |

FOREIGN PATENT DOCUMENTS 0425448  2/1991  European Pat. Off. .

Primary Examiner—Paul J. Hirsch
Attorney, Agent, or Firm—A. Nicholas Trausch

[57] ABSTRACT

This invention pertains to an intravenous infusion set and in particular, a winged needle assembly used for venipuncture having an integral hollow tubular protective member to reduce accidental needle sticks from such infusion set. The tubular member has a slot engagable by the wing on the rotatable hub and needle. Once aligned, the winged hub is pulled back into the slot and disengages at a lock-out position. The lateral notch retains the hub and needle within the tubular member.

12 Claims, 4 Drawing Sheets

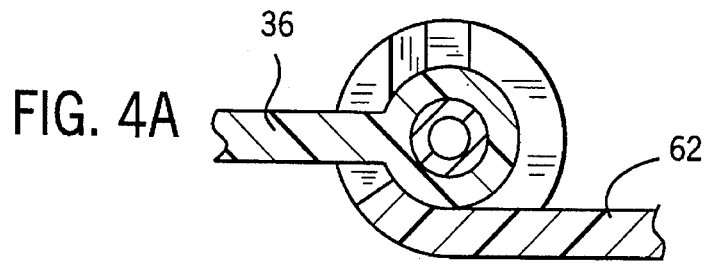
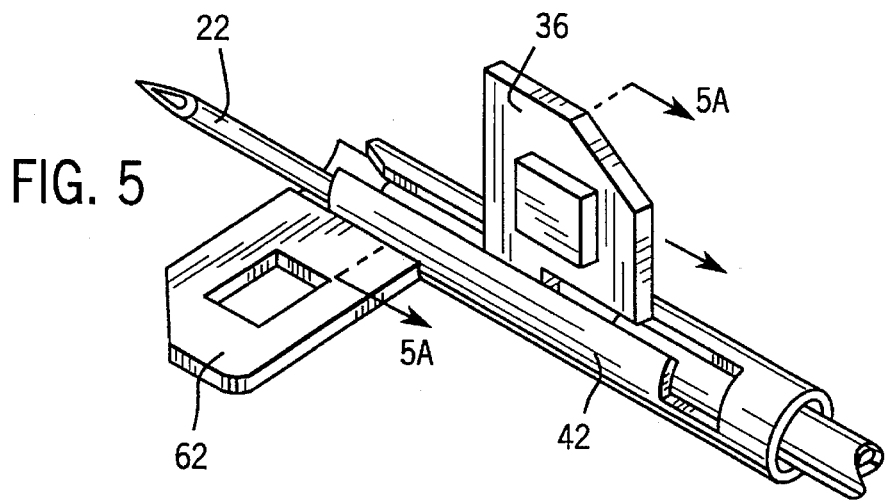
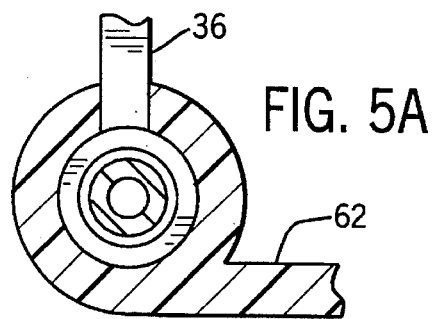
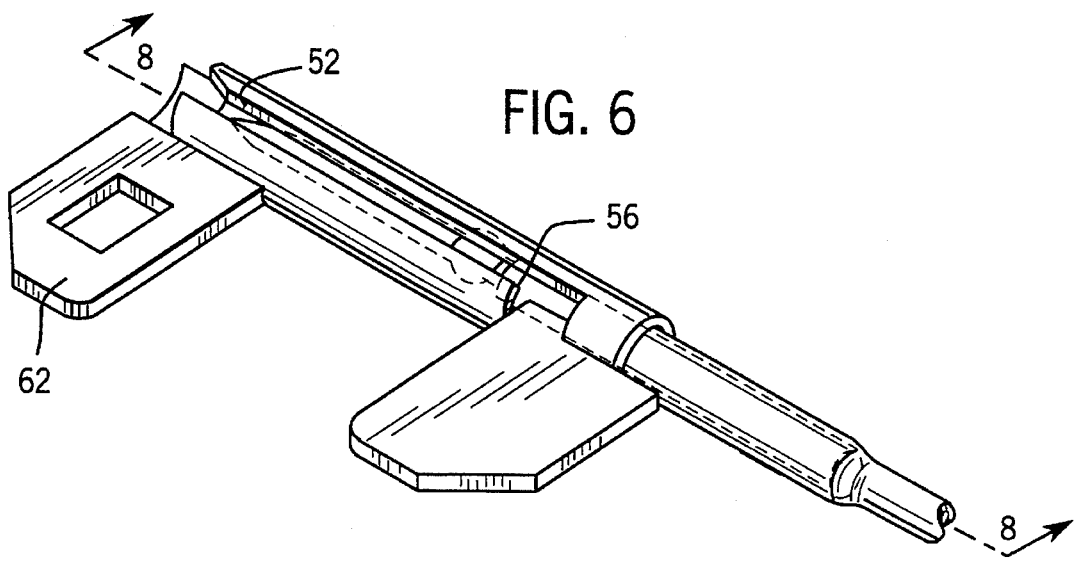

WINGED NEEDLE ASSEMBLY WITH PROTECTIVE MEMBER

FIELD OF THE INVENTION

The present invention generally relates to an intravenous (IV) infusion set and in particular, to a winged needle assembly usable for venipuncture that includes an integral protective member to reduce accidental needle stick from such infusion sets.

BACKGROUND OF THE INVENTION

Accidental stick from contaminated needles, syringes, and other sharp medical equipment contaminated by contact with an infected patient's bodily fluids pose a serious risk to healthcare workers. Proper disposal of "sharps" significantly reduces accidental stick. For example, standard procedures most often require used needles to be covered or recapped prior to disposal.

A sheath is provided to protect the needle point from damage prior to use and is often retained and refitted by the healthcare provider prior to disposal of the used needle. However, replacing a protective sheath requires the healthcare provider to align and push the sheath on the needle. This exposes the worker's hand to the sharp end of the needle and creates a new risk of needle stick injury. If the sheath is misplaced or lost, the needle is often disposed of without being covered.

Recently, certain safety devices for infusion sets have been developed to enclose or contain needles once they have been used. However most of these devices have limitations such as excessive size or require extra manipulation that frustrate their proper and easy use. For example, the devices described in U.S. Pat. Nos. 4,941,881, 5,069,341, and 5,330,438 are directed to protective sheaths that are slidably disposed on the IV tubing but require extra manipulation and/or are too bulky in size to be reliably and properly utilized.

The present invention overcomes the problems associated with prior procedures and the recently described devices and provides new advantages.

SUMMARY OF THE INVENTION

The intravenous needle assembly of the present invention includes a hollow needle having a sharp end, a rear end, and a fluid passageway there between. A cylindrical hub circumferentially secures the rear portion of the needle so that a portion of the needle including the sharp end projects forward from the hub. A first wing extends longitudinally and radially outward from the hub. A hollow, longitudinally extending tubular member having a front end, a rear end, and an axial bore is adapted to slidably receive the cylindrical hub. A longitudinal slot in the tubular member extends from the front edge to a lock-out position on the tubular member and is adapted to engage the extending first wing so that the longitudinal movement of the first wing in the slot controls the axially movement of the hub and needle within the bore of the hollow tubular member. The slot has a length from the front end to the lock-out position that is greater than the portion of the needle projecting forward from the hub. Thus, when the first wing is at the lock-out position of the slot, the sharp end of the needle is completely retracted within the hollow tubular member.

The invention also includes structure for automatically retaining the hub and the used needle within the hollow tubular member. In a preferred embodiment the retaining structure includes a lateral notch at the lock-out position of the slot that is adapted to automatically disengage the first wing from the slot and capture the first wing in the notch.

These and other objects, features, and advantages of this invention are evident from the following description of a preferred embodiment of this invention with reference to the accompanying drawings.

BRIEF DESCRIPTION OF THE DRAWINGS

FIG. 4A is an enlarged cross-sectional view along line 5A—5A in FIG. 4;

FIG. 5 is a perspective view of the winged needle assembly with the hub wing aligned in the longitudinal slot and the needle partially withdrawn into the protective member;

FIG. 5A is an enlarged cross-sectional view along line 5A—5A of FIG. 5;

FIG. 6 is a perspective view of the winged needle assembly after the needle has been withdrawn from the patient and completely retracted within the protective member and the hub wing disengaged from the longitudinal slot;

DETAILED DESCRIPTION OF THE PREFERRED EMBODIMENT

Figure 1:
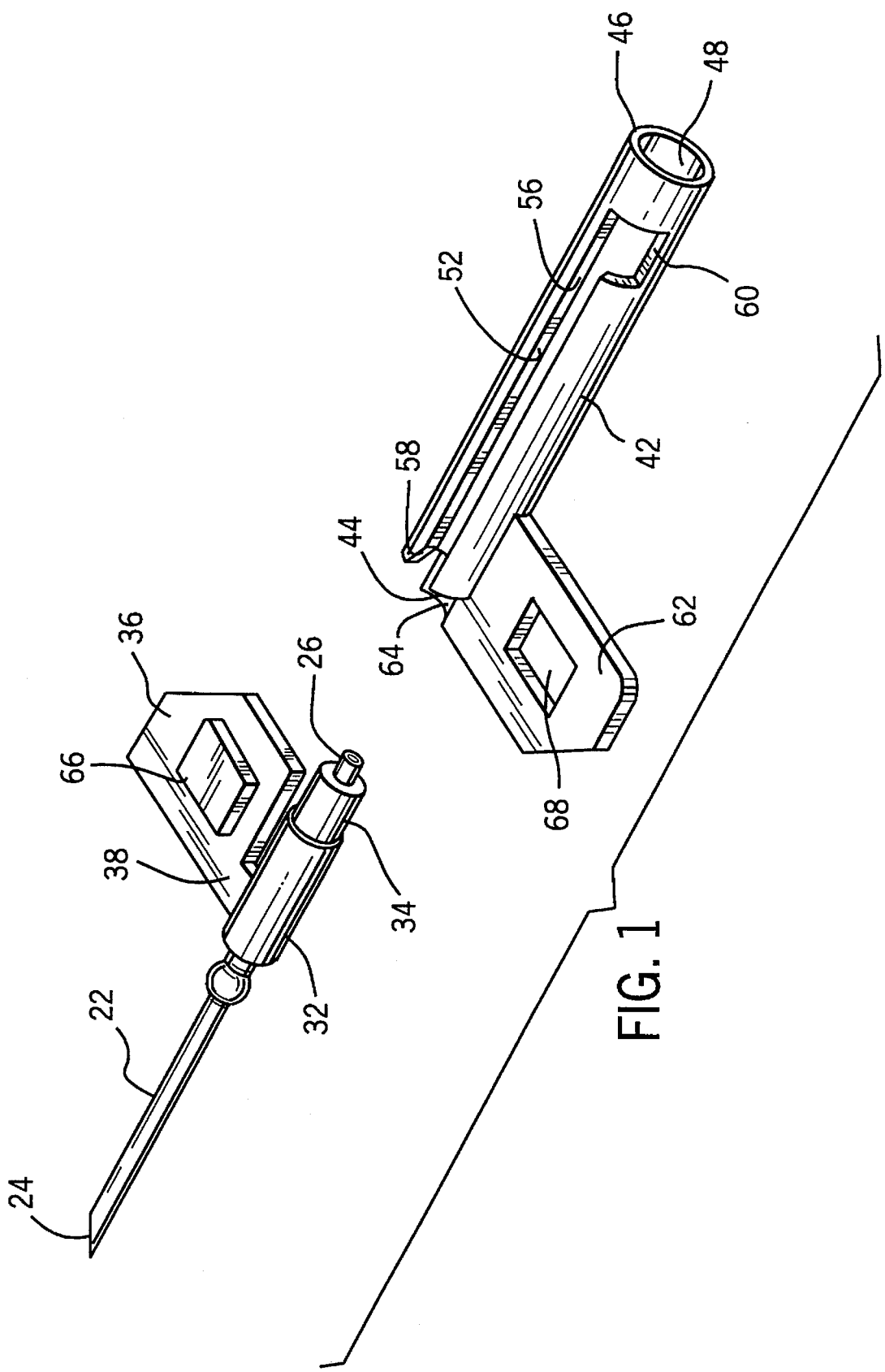
FIG. 1 is an exploded perspective view of the winged needle assembly of the present invention.

While the present invention is susceptible of embodiments in various forms, there is shown in the drawings and will hereinafter be described a presently preferred embodiment, with the understanding that the present disclosure is to be considered an exemplification of the invention, and is not intended to limit the invention to the specific embodiments illustrated.

Figure 2:
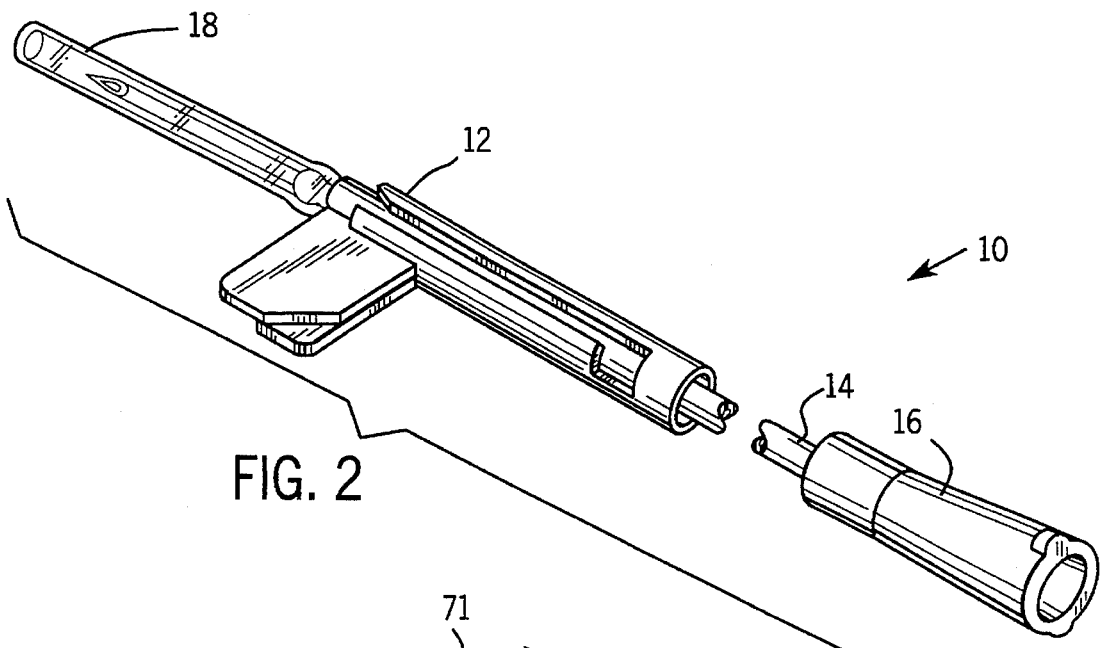
FIG. 2 is a perspective view of an IV infusion set prior to use including the winged needle assembly of the present invention.

An intravenous infusion set 10 having a winged needle assembly 12 according to the present invention is shown in FIG. 2. The infusion set also includes a section of hollow medical tubing 14, a standard fluid connector 16 and a removable sheath 18 covering the needle. A conventional female luer fitting is shown although other standard fluid connectors such as a male adapter plug, for example, are also suitable for fluidly connecting the set to a fluid source.

The winged needle assembly 12 of the present invention is best understood with reference to FIG. 1. The needle assembly 12 includes a hollow needle 22 having a sharp end 24. The sharp end is preferably beveled. The hollow needle is manufactured of stainless steel and has a fluid passageway between the front end 24 and the rear end 26.

A cylindrical hub 32 circumferentially secures a rear portion of the needle. The hub is preferably molded of a resilient plastic such as a medical grade polypropylene or polyvinylchloride. The hub 32 may be molded with the needle 22 in place or the needle may be secured to a molded hub in a subsequent assembly step. The rear end of the hub is constructed with a reduced diameter portion 34 for connecting the medical tubing 14 to the fluid passageway of the needle 22. The medical tubing 14 is permanently attached to the hub 32 by a solvent bond at 34 for example. The tubing 14 may form a slight outward radial shoulder at the juncture with the hub. The purpose of this shoulder will be pointed out in the description that follows.

A first wing 36 extends longitudinally and outward front the hub 32. The wing 36 is radially attached to the hub and is of sufficient size to be easily grasped by a healthcare provider between the thumb and the first finger to firmly control placement of the sharp end of the needle extending from the hub 32. The wing is preferably connected to the hub by a small stem portion 38 that has a longitudinal length which is less than the length of the wing 36. By minimizing the portion of the wing that is directly attached to the hub the overall length of the needle assembly 12 becomes shorter, as will be apparent from the description that follows. The stem portion 38 has generally the same thickness as the wing 36 to provide a solid connection of the wing 36 to the hub 32. The wing 36 and stem 38 are preferably integrally manufactured with the hub 32 as one piece by a plastic injection mold process for example.

A hollow tubular protective member 42 has a front end 44, a rear end 46, and an axial bore 48. The protective member 42 is also preferably manufactured from a moldable medical grade plastic. The axial bore 48 of the protective member 42 is constructed with an inner diameter of sufficient size to slidably receive the cylindrical hub 32 and tubing 14. Thus, enough clearance is provided between the inner diameter of the bore 48 and the outer diameter of the cylindrical hub 32 or tubing 14 to allow the hub and tubing to slide axially within the bore.

The protective member 42 also includes a longitudinal slot 52 that extends through the tubular surface of the hollow member and into the axial bore 48. The slot 52 extends longitudinally from the front end 44 of the protective member to a lock-out position 56 that is located forward of the rear end 46.

The longitudinal slot 52, as manufactured and before further assembly, has a predetermined slot width configuration. The predetermined slot width is wide at the front end 44 of the tubular member to facilitate entry of the first or hub wing 36 into the slot. The predetermined slot width is narrow at the lock-out position 56 to resist re-entry of the hub wing into the slot. Preferably, the predetermined slot width converges inward from the front end 44 of the slot to a minimal width at the lock-out position 56. The predetermined slot width at the lock-out position 56 is always less than the thickness of the engaged wing 36 or stem portion 38. Optimally, the preselected slot width at the lock-out position 56 is zero. That is, the opposite sides of the slot are in touching contact, and the slot closes on itself.

Because of the longitudinal split created by the slot 52, the tubular protective member 42 has certain spring characteristics. These characteristics allow the slot width as manufactured to increase to accommodate the thickness of the wing 36 or stem portion 38.

Thus, the spring characteristics of the split plastic tubular member 42 creates an effective slot width to accommodate the thickness of the wing 36 or the stem portion 38. The effective slot width will not cause the wing or stem to bind in the slot as the hub 32 moves through the axial bore 48.

The longitudinal slot 52 has a length from the front end 44 to the lock-out position 56 that is greater than the length of the exposed portion of the needle 22 projecting forward from the hub 32. Thus, when the first wing 36 is moved to the lock-out position 56 in the slot, the sharp end 24 of the needle is completely retracted within the protective member 42.

A lateral notch 60 is constructed at the lock-out position 56. The lateral notch 60 automatically disengages the wing or stem portion from the slot after the trailing edge of the wing or stem portion passes the lock-out position 56. The lateral notch 60 is constructed with a radial dimension that is greater than the thickness of the wing or stem portion. The lateral notch 60 is also constructed with a longitudinal length greater than the length of the wing 36 or stem portion 38. Thus, when the trailing edge of the wing or stem to moves past the lock-out position 56 and into the lateral notch 60, the wing or stem portion is no longer engaged in the slot 52. The resiliency of the stretched tubular member 32 causes the longitudinal slot 52 to spring back to the manufactured predetermined slot width. At the lock-out position 56, the slot contracts to the minimal preselected slot width that is less than the thickness of the wing or stem portion. The lateral notch 60 captures the wing or stem portion and prevents either forward or rearward movement of the wing 36 or stem 38. Thus the needle 22 is retained in the protective member 32.

Since the longitudinal slot 52 does not extend the full length of the protective member 32, the lateral notch 60 prevents the wing or stem from sliding completely out the back of the protective member, which would expose the needle point 24.

The longitudinal slot 52 also includes a tapered lead-in portion 58 at the front end 44 of the protective member 42 to facilitate initially engaging the wing 36 or stem portion 38 in the slot The protective member 42 also includes a second wing 62 that extends longitudinally and outward along the front of the hollow tubular member. The second wing 62 extends in the opposite direction of the first wing 36 and is radially perpendicular to the slot 52.

The second wing 62 is positioned forwardly offset from the front end 44 of the tubular member to create an open semi-circular arc portion 64 at the front of the hollow member 42. The open arc portion 4 has generally the same or greater length as the wing 36 or stem portion 38 and allows the wing or stem portion 38 to rotate freely through an arc of 180°. Thus, the first wing 36 can rotate from abutting contact with the second wing 62 to a position directly opposite the fixed orientation of the second wing. Preferably, at a perpendicular position or approximately midway through the 180° arc, the first wing 36 rotates into alignment with the tapered lead-in portion 58 of the longitudinal slot 52.

The lateral notch 60 extends radially from the longitudinal orientation of the slot in the direction of the second wing 62. The lateral notch arc portion is approximately 90° and allows the first wing 36 or stem portion 38 to be rotated into flat alignment with the second wing 62 for disposal.

The two wings 36 and 62 also include a projection 66 and a recess 68 for temporarily securing the wings together. The wings are secured together to increase needle placement control during the venipuncture step described below. The wings also include diagonally opposite cut-off portions 70 and 71 to assist in separating the temporarily secured wings.

Figure 7:
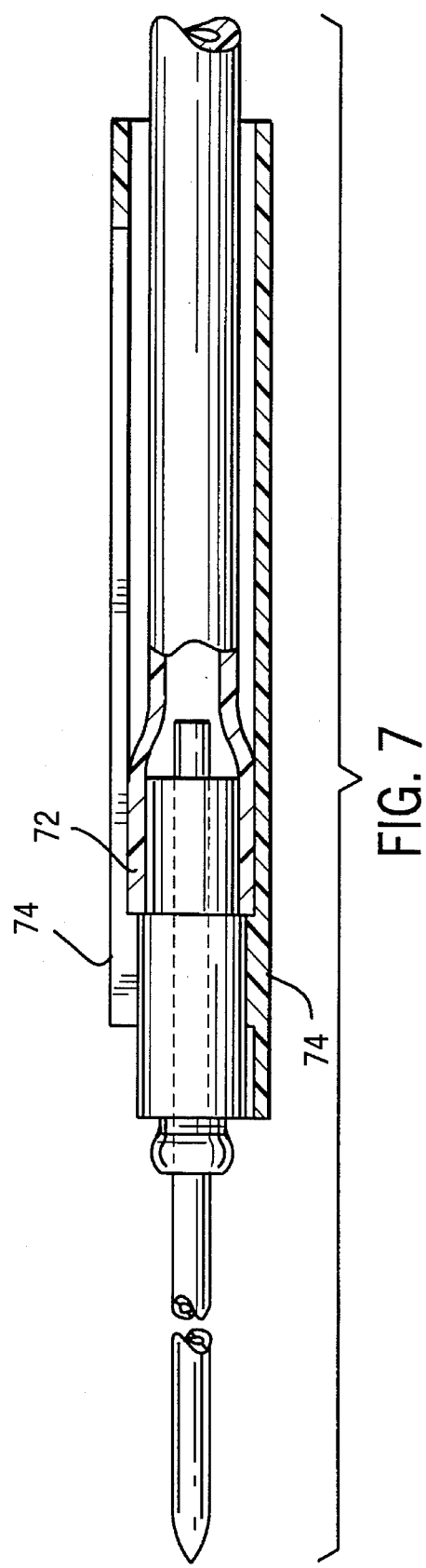
FIG. 7 is a longitudinal cross-section view along the line 7—7 in FIG. 4.
Figure 8:
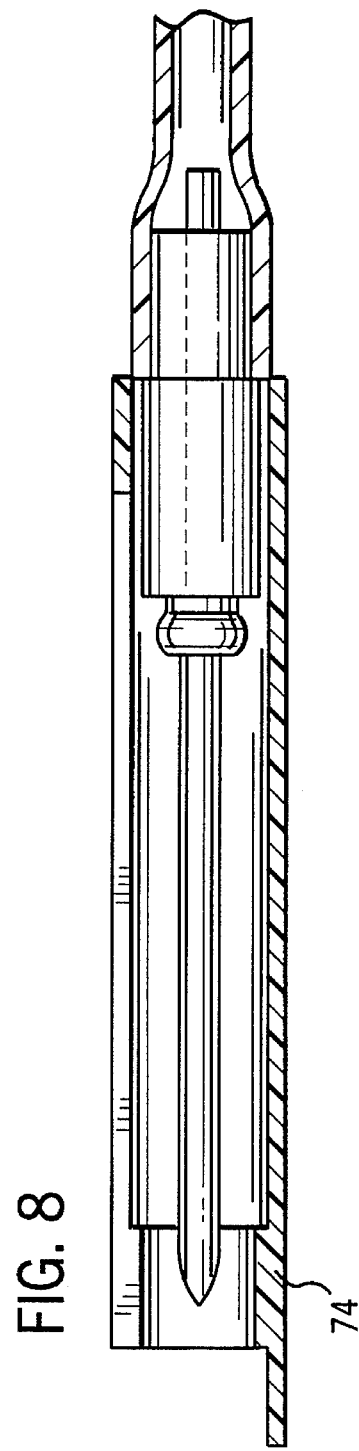
FIG. 8 is a longitudinal cross-section view along line 8—8 in FIG. 6.

When the winged needle assembly is initially assembled, the unconnected tubing 14 is inserted through the rear end 46 and out the front end 44 of the tubular member. The tubing is bonded to the reduced diameter portion 34 of the hub. As previously described, the tubing may have a slightly larger outer diameter at the juncture with the hub than the hub outer diameter. This shoulder 72 is best seen in FIG. 7.

Also the hollow tubular member 42 is preferably constructed with a reduced inner diameter annular portion 74 at the front end 44. The reduced diameter portion initially locates the wing 36 or stem portion 38 of the hub at the open semi-circular arc portion 64. The reduced diameter portion 74 abuts against the shoulder 72 and prevents the hub and needle from sliding axially forward out of the tubular member from the initial position.

A venipuncture procedure that utilizes the winged needle assembly of the present invention will now be described. The winged needle infusion set is conventionally packaged in a sterile blister package (not shown) with the open end sheath 18 covering the sharp end of the needle 22, as shown in FIG. 2. As previously described, a section of medical tube 14 and a fluid connector 16 such as a female luer connector are attached to the rear end of the needle assembly. The two wings 36 and 62 are initially folded and secured together. The connector 16 is removed from the packaging and attached in an aseptic manner to a source of fluid. The wing needle infusion set is then primed with the sheath 18 in place.

Figure 3:
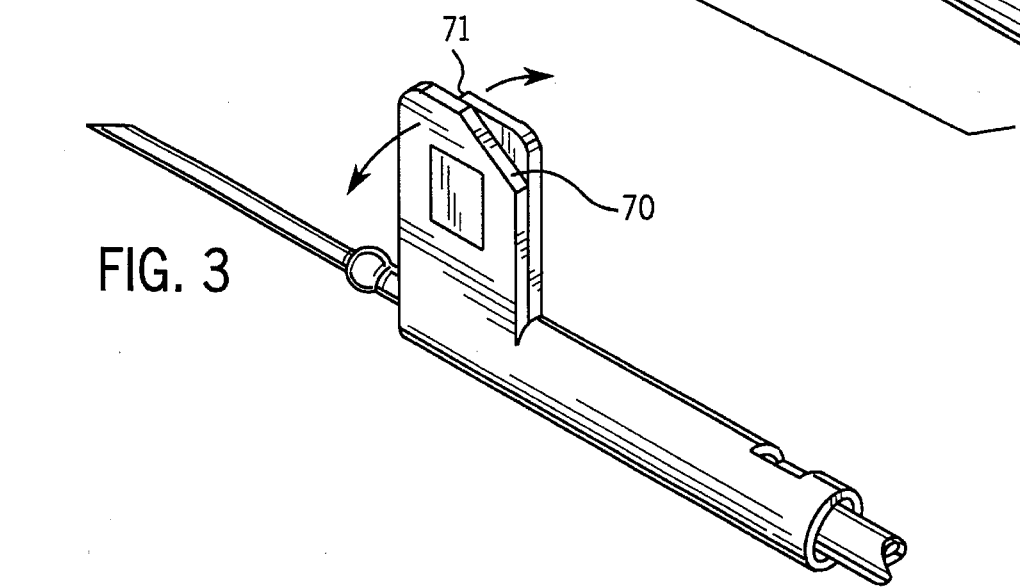
FIG. 3 is a perspective view of the winged needle assembly with the sheath removed and the needle oriented for insertion into a patient's vein.

The healthcare provider then grasps the secured wings between the thumb and first finger. As shown in FIG. 3, the needle 22 is in a bevel-up orientation and is readily inserted into a vein of the patient after the sheath is removed.

Figure 4:
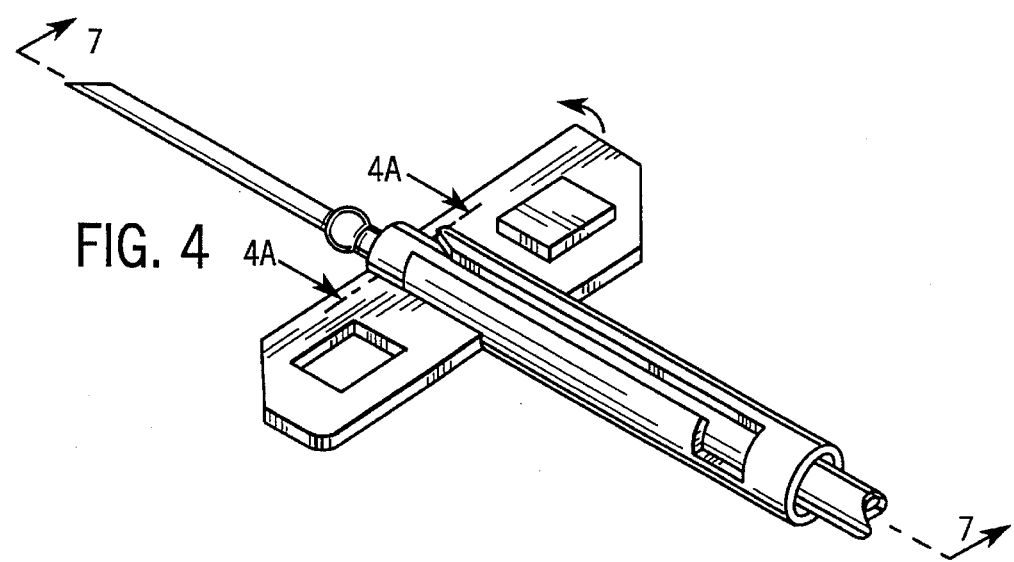
FIG. 4 is a perspective view of the winged needle assembly with the wings spread flat for securing to a patient during an IV infusion procedure.

As shown in FIG. 4, once the needle 22 is properly positioned in the vein, the two wings are rotated opposite to one another until they are in a flat orientation in contact with the patient's skin. The wings are then secured by tape to the patient's skin to minimize needle movement.

To safely remove the winged needle infusion set from the patient, the securing tape is removed. As shown in FIG. 5, the wing 62 integral with the hollow tubular member 42 is then pressed against the skin and the wing 36 integral with the hub is rotated into alignment with the longitudinal slot 52. The tapered lead-in portion 58 at the front end of the slot 52 facilitates alignment and entry of the wing 36 or stem portion of the wing 36 into the slot. The medical tubing 14 connected to the winged needle assembly 12 is then pulled back, which pulls the wing 36 or stem portion 38 through the slot 52 and withdraws the needle 22 from the vein and into the hollow tubular protective member 42.

When the wing or stem portion 38 reaches the lateral notch 60 at the lock-out position of the slot, the wing or stem automatically disengages from the slot. The resiliency of the plastic material of the partially split tubular member 42 causes of the slot 52 to substantially close on itself as seen at the lock-out position 56 in FIG. 6. The substantially closed slot prevents the wing or stem portion 38 from reengaging in the slot and thus prevents the sharp end of the needle from moving out of the protective member 42.

As a further precaution and to reduce the profile of the used needle assembly, the wing 36 can be rotated in the lateral notch into flat alignment with wing 62. The winged needle infusion set 10 is now ready for safe disposal with the needle retained in the tubular member thus reducing further risk of accidental needle stick injury.

A key advantage of the present invention is that the sharp end 24 of the needle 22 is never exposed after it is inserted into the patient's vein. The needle is pulled directly into the hollow tubular member 42 as it is withdrawn from patient's vein.

Another advantage of the present invention is that the lateral notch 60 at the lock-out position 56 of the longitudinal slot 52 automatically disengages the wing or stem portion from the slot. The lateral notch 60 further retains the wing or stem portion from reengaging in the slot, thus retaining the sharp end of the needle in the protective member.

Another key advantage of the present invention is that the protective member 42 is integrally assembled to the winged needle infusion set. Integral attachment eliminates the possibility of the protective member being lost or not attached and thus not used by the healthcare provider. Also, the location of the protective member immediately adjacent and in line with the rear portion of the needle 22 and the ease of use greatly increases the probability a contaminated needle will be properly enclosed in the protective member prior to disposal.

From the foregoing, it will be seen that numerous modification and variation can be affected without departing the true spirit and scope of the novel concept of the present invention. It is to be understood that no limitation with respect to the specific embodiments is intended or should be inferred. The disclosure is intended to cover all such modification as fall within the scope of the appended claims.

What is claimed is:

1. An intravenous needle assembly, comprising:

a hollow needle having a front portion with a sharp end and a rear portion;

a cylindrical hub for securing the rear portion of the needle so that the front portion of the needle projects axially forward from the hub;

a first wing radially attached to the hub and extending longitudinally parallel to the needle;

a hollow, longitudinally extending tubular member having a front end, a rear end, and an axial bore for axial movement of the cylindrical hub within the bore;

a longitudinal slot in the hollow tubular member extending from the front end to a lock-out position, the first wing engagable in the slot for longitudinal movement of the first wing in the slot to control the axially movement of the hub within the bore of the hollow tubular member; and a second wing extending longitudinally outward from the front end of the hollow tubular member, the second wing being radially perpendicular to the longitudinal slot.

2. The intravenous needle assembly of claim 1 wherein the slot has a longitudinal length from the front end to the lock-out position that is greater than the length of the front portion of the needle projecting forward front the hub so that when the first wing of the hub is moved past the lock-out position of the slot, the sharp end of the needle is within the hollow tubular member.

3. The intravenous needle assembly of claim 2 further including means for retaining the hub and needle within the hollow tubular member.

4. The intravenous needle assembly of claim 3 wherein the retaining means is a lateral notch at the lock-out position of the slot for disengaging the first wing from engagement in the slot.

5. The intravenous needle assembly of claim 4 wherein the slot has a resiliently expandable width caused by the construction of the tubular member.

6. The intravenous needle assembly of claim 5 further including an open semi-circular arc portion at the front end of the hollow tubular member to allow the first wing to rotate from a longitudinal orientation in abutting contact with the second wing to an opposite longitudinal orientation.

7. The intravenous needle assembly of claim 6 wherein the lateral notch extends radially between the longitudinal orientation of the slot and the longitudinal orientation of the second wing segment.

8. The intravenous needle assembly of claim 7 further including a stem portion for radially attaching the first wing to the hub, wherein stem portion has a length less than length of the open arc portion and length of the lateral notch.

9. The intravenous needle assembly of claim 8 further including means in the hollow tubular member for initially locating the stem portion of the first wing at the semi-circular arc portion.

10. The intravenous needle assembly of claim 9 further including means for securing the first wing to the second wing when the first and second wings are in abutting contact.

11. The intravenous needle assembly of claim 10 further including means for separating the first wing from the second wing when the wings are in abutting contact and secured by the securing means.

12. The intravenous needle assembly of claim 11 further including means attached to the cylindrical hub for fluid flow communication with the rear portion of the needle.

\* \* \* \* \*

UNITED STATES PATENT AND TRADEMARK OFFICE
CERTIFICATE OF CORRECTION

PATENT NO.    :   5,498,241
DATED         :   March 12, 1996
INVENTOR(S)  :   R. C. Fabozzi It is certified that error appears in the above-indentified patent and that said Letters Patent is hereby corrected as shown below:

Column 6, line 54, change "front" to --from--.

Signed and Sealed this

Nineteenth Day of November, 1996

Attest:

BRUCE LEHMAN

*Attesting Officer*      *Commissioner of Patents and Trademarks*